United States Patent
Huang et al.

(10) Patent No.: US 12,260,517 B2
(45) Date of Patent: Mar. 25, 2025

(54) OPTICAL SYSTEM AND OPTICAL IMAGE PROCESSING METHOD USING IMAGE RESTORATION

(71) Applicant: NATIONAL CENTRAL UNIVERSITY, Taoyuan (TW)

(72) Inventors: Chen Han Huang, Taoyuan (TW); Chun San Tai, Taoyuan (TW); Ting Yi Lin, Taoyuan (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 697 days.

(21) Appl. No.: 17/543,730

(22) Filed: Dec. 7, 2021

(65) Prior Publication Data
US 2022/0188981 A1 Jun. 16, 2022

Related U.S. Application Data

(60) Provisional application No. 63/124,220, filed on Dec. 11, 2020.

(51) Int. Cl.
*G06T 5/00* (2024.01)
*G01R 33/56* (2006.01)
(Continued)

(52) U.S. Cl.
CPC .............. *G06T 5/00* (2013.01); *G01R 33/56* (2013.01); *G06T 3/40* (2013.01); *G06T 5/50* (2013.01);
(Continued)

(58) Field of Classification Search
CPC .... G06T 5/00; G06T 3/40; G06T 5/50; G06T 2207/10056; G06T 2207/20081;
(Continued)

(56) References Cited

U.S. PATENT DOCUMENTS

2004/0130781 A1* 7/2004 Shinohara .............. G02B 21/16
359/383
2007/0093993 A1* 4/2007 Stork ..................... H04N 23/00
703/2
(Continued)

FOREIGN PATENT DOCUMENTS

| CN | 111583166 A | 8/2020 |
| CN | 109884018 B | 9/2020 |
(Continued)

OTHER PUBLICATIONS

Gaocheng Yu et al. "Efficient Progressive High Dynamic Range Image Restoration via Attention and Alignment Network" Apr. 2022, IEEE (Year: 2022).*
(Continued)

*Primary Examiner* — John Villecco
*Assistant Examiner* — Alejandro Hernandez

(57) ABSTRACT

Disclosed is an optical system using image restoration, including a light source, a pinhole, a testing platform, an image sensor and an image processing device. The pinhole is disposed on a light transmission path of the light source. The testing platform is disposed on the light transmission path of the light source and the pinhole is located between the light source and the testing platform. The testing platform is used to place a testing sample. The image sensor is disposed below the testing platform, and used to sense the testing sample so as to output an optical diffraction signal. The image processing device is electrically connected to the image sensor and used to perform signal processing and optical signal recognition on the optical diffraction signal of the testing sample so as to obtain a clear image of the testing sample.

7 Claims, 5 Drawing Sheets

(51) Int. Cl.
*G06T 3/40* (2024.01)
*G06T 5/50* (2006.01)
*G06V 10/40* (2022.01)
*G06V 10/80* (2022.01)
*G06V 10/82* (2022.01)
*G06V 20/69* (2022.01)
*G16H 10/40* (2018.01)
*G16H 30/40* (2018.01)
*H04N 23/56* (2023.01)

(52) U.S. Cl.
CPC ............ *G06V 10/40* (2022.01); *G06V 10/806* (2022.01); *G06V 10/82* (2022.01); *G06V 20/693* (2022.01); *G06V 20/695* (2022.01); *G16H 10/40* (2018.01); *G16H 30/40* (2018.01); *H04N 23/56* (2023.01); *G06T 2207/10056* (2013.01); *G06T 2207/20081* (2013.01); *G06T 2207/20084* (2013.01); *G06T 2207/20221* (2013.01); *G06T 2207/30024* (2013.01); *G06V 2201/03* (2022.01)

(58) Field of Classification Search
CPC . G06T 2207/20084; G06T 2207/20221; G06T 3/4046; G06T 3/4053; G06T 7/0012; G16H 10/40; G16H 30/40; G06V 20/695; G06V 10/806; G06V 10/40; G06V 10/82; G06V 20/693; G06V 2201/03; G06V 20/69; H04N 23/56; G01R 33/56; G02B 21/0032; G02B 21/365; G06N 3/08

See application file for complete search history.

(56) References Cited

U.S. PATENT DOCUMENTS

| | | | |
|---|---|---|---|
| 2009/0018414 A1* | 1/2009 | Toofan | A61B 5/0059 600/473 |
| 2011/0222056 A1* | 9/2011 | Seo | G01J 3/0205 356/302 |
| 2014/0375792 A1* | 12/2014 | Yaqoob | G01N 21/453 348/79 |
| 2015/0003592 A1* | 1/2015 | Beckers | G01N 23/20008 378/74 |
| 2017/0016768 A1* | 1/2017 | Golub | H04N 23/843 |
| 2017/0059408 A1* | 3/2017 | Körner | G01J 3/0229 |
| 2018/0143415 A1* | 5/2018 | Hollricher | G02B 21/36 |
| 2018/0149847 A1* | 5/2018 | Lytle | G02B 21/0076 |
| 2018/0157023 A1* | 6/2018 | Gunderson | G02B 21/26 |
| 2018/0173160 A1* | 6/2018 | Rosen | G01B 9/02097 |
| 2019/0294108 A1* | 9/2019 | Ozcan | G06V 10/82 |
| 2019/0362120 A1* | 11/2019 | Yeke Yazdandoost | H01L 27/14678 |
| 2021/0073959 A1 | 3/2021 | Elmalem et al. | |
| 2022/0188981 A1* | 6/2022 | Huang | G06V 10/40 |
| 2024/0264423 A1* | 8/2024 | Huang | G02B 21/365 |

FOREIGN PATENT DOCUMENTS

| | | | | |
|---|---|---|---|---|
| CN | 111917964 A | | 11/2020 | |
| CN | 112505911 A | | 3/2021 | |
| CN | 113031302 A | * | 6/2021 | ............ G02B 30/30 |
| JP | 2011191158 A | * | 9/2011 | |
| TW | 201428339 A | | 7/2014 | |
| WO | 2019200289 A1 | | 10/2019 | |

OTHER PUBLICATIONS

Yonglian Tang et al. "Deep Inception-Residual Laplacian Pyramid Networks for Accurate Single-Image Super-Resolution", Jun. 28, 2019, IEE (Year: 2019).*

* cited by examiner

OPTICAL SYSTEM AND OPTICAL IMAGE PROCESSING METHOD USING IMAGE RESTORATION

FIELD OF THE INVENTION

The present disclosure relates to an optical system and an optical image processing method, and in particular, to an optical system and an optical image processing method using deep learning image restoration.

BACKGROUND OF THE INVENTION

An optical microscope plays a very important role in the field of engineering physics or biomedicine. The optical microscope may be used to observe surface structures, cells or microorganisms that are invisible to naked eyes. In the field of laboratory medicine, major hospitals also rely heavily on an optical imaging technology in the diagnosis of diseases, such as various types of cancer or infectious diseases. It is necessary to observe a biopsy or a blood smear to evaluate whether cells are in a lesion state. However, a current optical imaging platform is limited in practical application due to complexity and high cost and must also be operated by trained laboratory personnel. The widespread application of the optical imaging platform is limited, especially in remote and limited regions.

Deep learning is a learning method that uses a large amount of data to train a constructed calculation model so as to extract data features. The amount of data in a training data set is an important condition for judging whether a training effect is good or bad. If the data in the training set is insufficient, even if the trained network model is capable of accurately predicting the trained data, the accuracy of predicting unknown data may be far lower than that of predicting the training set. Such a situation is called overfitting. It is not easy to obtain a large data set especially in the related fields of biomedicine. In order to solve the problem of insufficient data, data augmentation has become an important means to solve this problem.

Therefore, there is a need to apply a general lensless optical imaging technology in combination with data augmentation, so that the technology has the functions of miniaturizing a microscopic effect and greatly improving an image field of view, and can also achieve the efficacy of the optical microscope.

SUMMARY OF THE INVENTION

A main object of the present disclosure is to provide a system for lensless optical image restoration and a calculation method, which have the functions of miniaturizing a microscopic system and greatly improving an image field of view, perform image reconstruction using a deep learning algorithm, and can implement an automatic recognition function.

According to the above object, the present disclosure discloses an optical system using image restoration, including a light source, a pinhole, a testing platform, an image sensor and an image processing device. The pinhole is disposed on a light transmission path of the light source. The testing platform is disposed on the light transmission path of the light source and the pinhole is located between the light source and the testing platform. The testing platform is used to place a testing sample. The image sensor is disposed below the testing platform, and used to sense the testing sample so as to output an optical diffraction signal. The image processing device is electrically connected to the image sensor and used to perform signal processing and optical signal recognition on the optical diffraction signal of the testing sample so as to obtain a clear image of the testing sample.

Another object of the present disclosure is to provide an optical image processing method using an image restoration technology of deep learning, which can perform image reconstruction by means of a deep learning algorithm without an optical lens and can implement an automatic recognition function.

According to the above object, the present disclosure discloses an optical image processing method using image restoration, including: inputting a clear image and a plurality of optical diffraction signals of a testing sample into an image processing device of an optical image system for image reconstruction and predictive recognition; placing a testing sample to be examined on a testing platform, and sensing the optical diffraction signal of the testing sample via a light source dimmer and a pinhole through an image sensor; extracting a plurality of initial features of the testing sample through an image feature extraction module, extracting a plurality of image features of the optical diffraction signal of the testing sample through a residual network module according to the plurality of initial features, and performing upsampling through an image reconstruction module according to the plurality of image features of the optical diffraction signal extracted by the residual network module so as to restore an original resolution of the optical diffraction signal of the testing sample; and fusing the plurality of image features of the testing sample through a concatenation module so as to obtain the clear image.

The present disclosure is advantageous in that a conventional expensive optical microscope can be replaced by the system for lensless optical image restoration and the calculation method according to the present disclosure, a final image reconstruction result can be obtained in a short time, and an image resolution and recognition are approximate to the effect of the optical microscope and a large image field of view.

DETAILED DESCRIPTION OF THE EMBODIMENTS

The technical means adopted by the present disclosure to achieve predetermined objects will be set forth below in conjunction with the drawings and preferred embodiments of the present disclosure.

Figure 1:
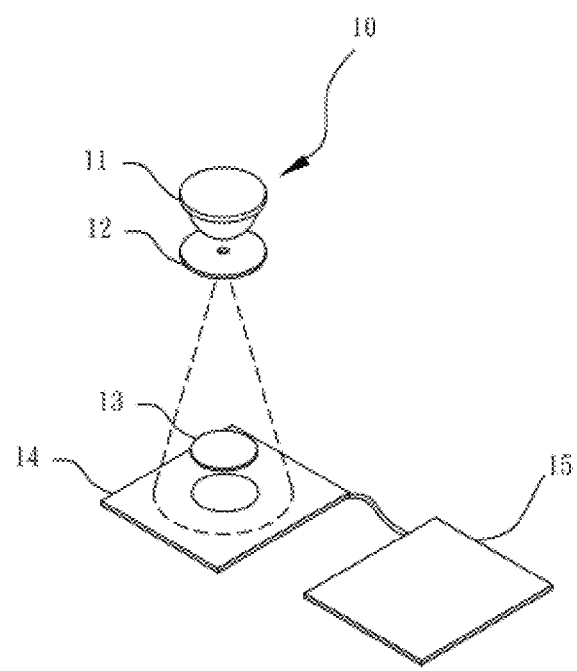
FIG. 1 is a schematic diagram of an optical system using image restoration according to the present disclosure.

FIG. 1 is a schematic diagram of an optical system using image restoration according to the present disclosure. As shown in FIG. 1, an optical system 10 using image restoration according to the present disclosure mainly includes a light source 11, a pinhole 12, a testing platform 13, an image sensor 14 and an image processing device 15.

The light source 11 may be a Light Emitting Diode (LED), etc., and a wavelength of the adopted light source 11 may be replaced, or a broad-wavelength light source (e.g. white light) may be used. A filter is further disposed in the optical system 10 of the present disclosure for wavelength selection, which is, however, not limited thereto. The pinhole 12 is disposed on a light transmission path of the light source 11. The pinhole 12 is an optical pinhole, is micron-sized, and may be constructed using a micron pinhole or an optical fiber, etc. The testing platform 13 is disposed below the pinhole 12, and located on the light transmission path passing through the pinhole 12. A testing sample to be tested is disposed on the testing platform 13. The testing sample may be a biopsy or a blood smear, which is, however, not limited thereto. The light source 11 transmits light to the pinhole 12 so as to collectively transmit the light to the testing platform 13, the light passes through the testing sample placed on the testing platform 13, and then an image of the testing sample is sensed by the image sensor 14. The image of the testing sample sensed by the image sensor 14 is a diffraction image, and the resolution and definition thereof are not suitable for medical examination. Therefore, the image of the testing sample obtained by the image sensor 14 needs to be further processed so that the resolution and definition of the image thereof may be used for medical examination.

For example, the present disclosure selects data augmentation modes including image translation, rotation and inversion based on the type of a sample target, an angle difference during shooting, optical diffraction signal reconstruction, etc. The manner of translation is to perform horizontal movement of an image randomly up, down, left and right within the range of not more than ten percent of the size of an input image. The rotation is to rotate an image at a random angle within 360 degrees from a center point of the image. The inversion is to invert an image as a mirror image left, right or up and down. In a calculation process of practical training of a deep learning image reconstruction model, an input optical diffraction signal and an image under a traditional microscope corresponding to the image are subjected to data augmentation with new random parameters in each training cycle. It means that although the same training data set is input in each training cycle, the data translation, rotation and inversion are performed again on a blood cell image at the beginning of each training cycle, so that the existing data set can be used more effectively in the training of the model, and the generalization ability of the model is greatly enhanced. When the model is evaluated with a validation set, it can be found that the reconstruction effect of the model in the validation set on a target image is only slightly lower than that on the training set.

The image processing device 15 is electrically connected to the image sensor 14, receives the image of the testing sample, and performs image processing and image recognition on the image of the testing sample. The image processing device 15 may be a computer device, such as a computer or server, which is, however, not limited thereto. The image processing device 15 includes a supervised mechanical learning algorithm used by a mechanical learning machine, such as an artificial neural network, a convolutional neural network, a transposed convolution, a Mask Region-based Convolutional Neural Network (Mask R-CNN), a residual neural network (ResNet), a Feature Pyramid Network (FPN), a nearest neighbor interpolation, a bi-linear interpolation, a bi-cubic interpolation, a logistic regression, a k nearest neighbor, a support vector machine, a decision tree induction algorithm, a random forest algorithm and/or Bayesian classification algorithms, etc., which is, however, not limited thereto.

In addition, it is to be noted here that in the present disclosure, in the deep learning technology of the image processing device 15, image recognition of the clear image is performed first. For example, when the testing sample is a blood smear, a clear image is input, and the image processing device 15 recognizes image features such as white blood cells or red blood cells in the blood smear, a large amount of image data of the testing sample sensed by the image sensor 14 of the present disclosure is input, image recognition and image processing are performed through the large amount of image data, the image processing device 15 may filter noise in the image data generated by the image sensor 14 and enhance features in the image data, and the clear image is obtained finally.

Figure 2:
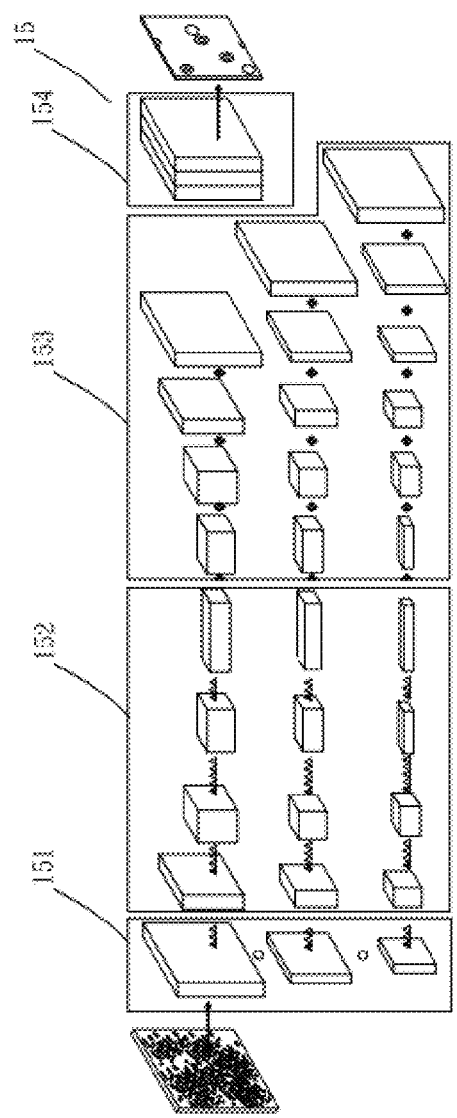
FIG. 2 is a block diagram of an image processing device according to the present disclosure.

As shown in FIG. 2, a main object of the image processing device 15 of the present disclosure is to reconstruct the optical diffraction signal recorded with intensity into an image observed under a microscope. The image processing device 15 is mainly divided into two parts: feature extraction (downsampling) and image reconstruction (upsampling). In a preferred embodiment of the present disclosure, feature training of the two parts adopts a convolutional neural network, and the image processing device 15 performs downsampling twice on a feature image during image input to form initial features of three parallel calculation sub-networks, in order to extract image (diffraction signal) features at different resolutions. Then, the features are extracted in parallel from the images with three different resolutions by taking the residual neural network (ResNet) as a backbone. Then, upsampling is performed gradually for different times according to different resolutions of sub-network extraction until the resolution of an original input image is restored. Finally, the restored features of the three sub-networks are concatenated and then processed by a convolutional neural network, so as to obtain a clear image as observed by the microscope.

In the present disclosure, different scales and advantageous features are searched for an image through a coding layer, and a series of convolutions and dimension reduction are performed on an input image. An overall architecture includes performing feature search on the image using a convolutional layer, and matching an activation layer to facilitate a deep learning model to learn a complex and non-linear output. In the present model, image features are extracted by means of a residual neural network composed of convolutional layers. A decoding layer is to perform upsampling step by step with a feature dimension symmetric to the coding layer, restore to an original input dimension, and output a reconstructed microscopic image.

Further, the image processing device 15 of the present disclosure includes an image feature extraction module 151, a residual network module 152, an image reconstruction module 153 and a concatenation module 154. The image feature extraction module 151 is mainly used to extract a plurality of initial features of a testing sample. The image feature extraction module 151 mainly performs an image processing step of downsampling in the field of deep learning. The residual network module 152 is connected to the image feature extraction module 151 and is used to extract a plurality of image features of an image of the testing sample according to the plurality of initial features. The image reconstruction module 153 is connected to the residual network module 152, and performs upsampling according to the image features of the image extracted by the residual network module 152 so as to restore an original resolution of the image of the testing sample. The concatenation module 154 is connected to the image reconstruction module 153, and the concatenation module 154 may fuse the plurality of image features of the testing sample so as to obtain the clear image.

In the image feature extraction module 151, when an optical diffraction signal is input, downsampling is firstly performed twice so as to obtain initial features of three parallel operation sub-networks of the optical diffraction signal, in order to extract image (diffraction pattern) features at different resolutions. A convolution operation of step 2 is used to replace a common pooling layer so as to reduce the loss of features. In the residual network module 152, when performing feature extraction, parallel feature extraction is performed on three sub-networks with images of different resolutions respectively by taking a residual network (ResNet50) as a backbone, and a series of convolution operations and dimension reduction are performed on the input optical diffraction signal, thereby searching for advantageous features at different scales. An overall architecture includes a convolutional layer, an activation layer and an addition layer. Features of the optical diffraction signal are firstly searched by the convolutional layer, the activation layer outputs the optical diffraction signal to perform linear rectification conversion to overcome the problem of gradient disappearance, and the optical diffraction signals which are originally input and non-linearly transformed are finally superimposed on the addition layer, so that a neural network can more effectively adjust the weight of a shallow network to make the gradient disappearance less likely to occur.

In the image reconstruction module 153, transposed convolution is used to perform upsampling step by step for different times according to different resolutions of sub-network extraction until the resolution of an original input image is restored. Nearest neighbor interpolation, bi-linear interpolation and bi-cubic interpolation are common methods in image dimension increase. However, compared with these methods, transposed convolution uses the neural network to learn better interpolation with the concept of convolution to improve the accuracy of image reconstruction. Finally, the features restored by the three sub-networks are fused in a concatenation manner in the concatenation module 154, which is different from the fusion of a plurality of features in the residual network using an addition manner in the case of no dimensional change. The concatenation manner retains more dimensional information, so that important features can be more freely selected from the features finally extracted by the convolutional layer at different resolutions, which is more advantageous in image reconstruction.

For example, still referring to FIG. 2, after receiving an input blood cell image from the image feature extraction module 151, the residual network module 152 will sequentially generate a plurality of images of feature maps through multiple times of downsampling. The downsampling manner used in the present disclosure is taking the residual network as a backbone, which includes a convolutional layer, an activation layer and an addition layer. By utilizing the cross-layer connection characteristic of the residual network, the network can be effectively deepened to perform feature search, and meanwhile, feature maps of various scales obtained through dimension reduction each time in the calculation process are saved, which is advantageous for subsequent image feature fusion. The image reconstruction module 153 adjusts the depth of a feature map image obtained by the residual network module 152 to obtain an image thereof through a convolution operation, performs upsampling on the image step by step through nearest neighbor upsampling, and performs feature fusion on images of each feature map obtained by the residual network module 152 respectively while upsampling, so that image feature information extracted by the residual network module 152 at different scales can be used more effectively.

In the process of feature fusion, in order to avoid an aliasing effect that may occur when the upsampling operation is performed in the image reconstruction module 153, i.e., a distortion phenomenon caused when the feature map is upsampled and pixels are filled. By performing a convolution operation on the feature map after the fusion of the residual network module 152 and the image reconstruction module 153, the distortion of image features can be greatly reduced, so as to obtain a plurality of feature maps, and max pooling is finally performed on the feature maps once. The max pooling means that a certain image is filtered to extract several feature values. Only the pooling layer with the largest feature value is taken as a reserved value, and all the other feature values are discarded. The maximum value represents that only the strongest feature is reserved, and other weak features are discarded, in order to obtain features with a smaller size so as to be combined to subsequently detect and position a large target object in the image.

After the concatenation module 154 obtains a final image feature map, each target detection object in the obtained image feature map is positioned, and a specific position of the target detection object in the image is marked by a square bounding box. In the concatenation module 154, important features are more freely selected from features extracted with different resolutions, which is more advantageous for image reconstruction.

Figure 3A:
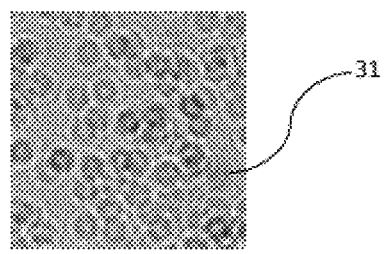
FIG. 3A is a schematic diagram of an optical diffraction signal sensed by an image sensor according to the present disclosure.
Figure 3B:
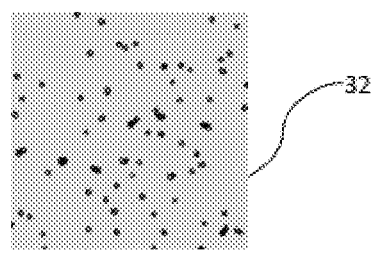
FIG. 3B is a schematic diagram of a clear image processed by an image processing device according to the present disclosure.
Figure 3C:
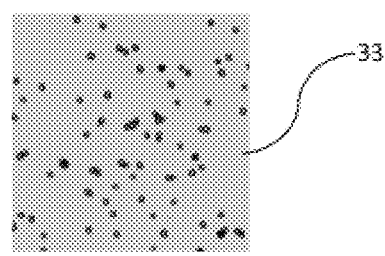
FIG. 3C is a schematic diagram of an image of an optical microscope.
Figure 3E:
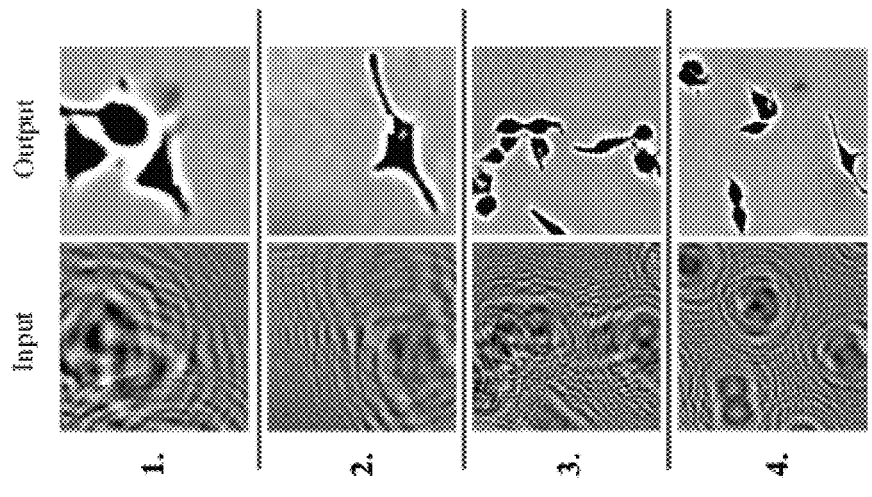
FIGS. 3D-3E are diagrams comparing an input image and a processed output image of an image processing device according to the present disclosure.
Figure 3D:
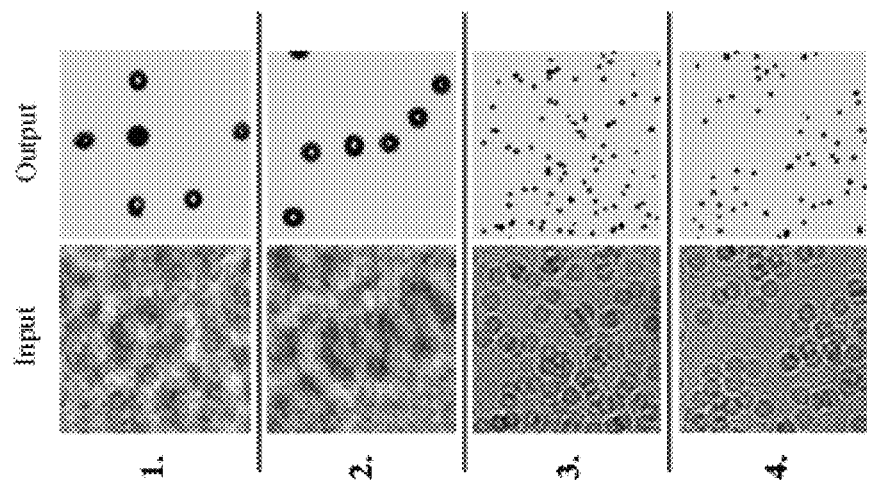

FIG. 3A is a schematic diagram of an optical diffraction signal sensed by an image sensor 14 according to the present disclosure. FIG. 3B is a schematic diagram of a clear image processed by an image processing device 15 according to the present disclosure. FIG. 3C is a schematic diagram of an image of an optical microscope. It is apparent from FIG. 3A that the image definition of the optical diffraction signal 31 sensed by the image sensor 14 is not good and white blood cells or red blood cells are not clearly visible, while it is apparent from FIG. 3B that the clear image 32 processed by the image processing device 15 of the present disclosure is much clearer than the optical diffraction signal 31 and has resolution and definition similar to an image 33 generated by the optical microscope shown in FIG. 3C. FIGS. 3D and 3E are diagrams comparing an input image and a processed output image of an image processing device according to the present disclosure. It is apparent from FIGS. 3D and 3E that the image processing device 15 of the present disclosure has reconstructed images of optical diffraction signals of a blood cell and a nasopharyngeal carcinoma cell, which cannot be distinguished by the type of the present disclosure, into images that can be clearly distinguished as a microscope. And the restored validation set images of the present disclosure are input into a model for deep learning, so as to realize the tasks of subsequent classification, positioning and mask generation of blood cell images.

By means of the optical system 10 using image restoration according to the present disclosure, a clear effect similar to that of an image generated by an optical microscope can be obtained without using an expensive optical microscope.

Figure 4:
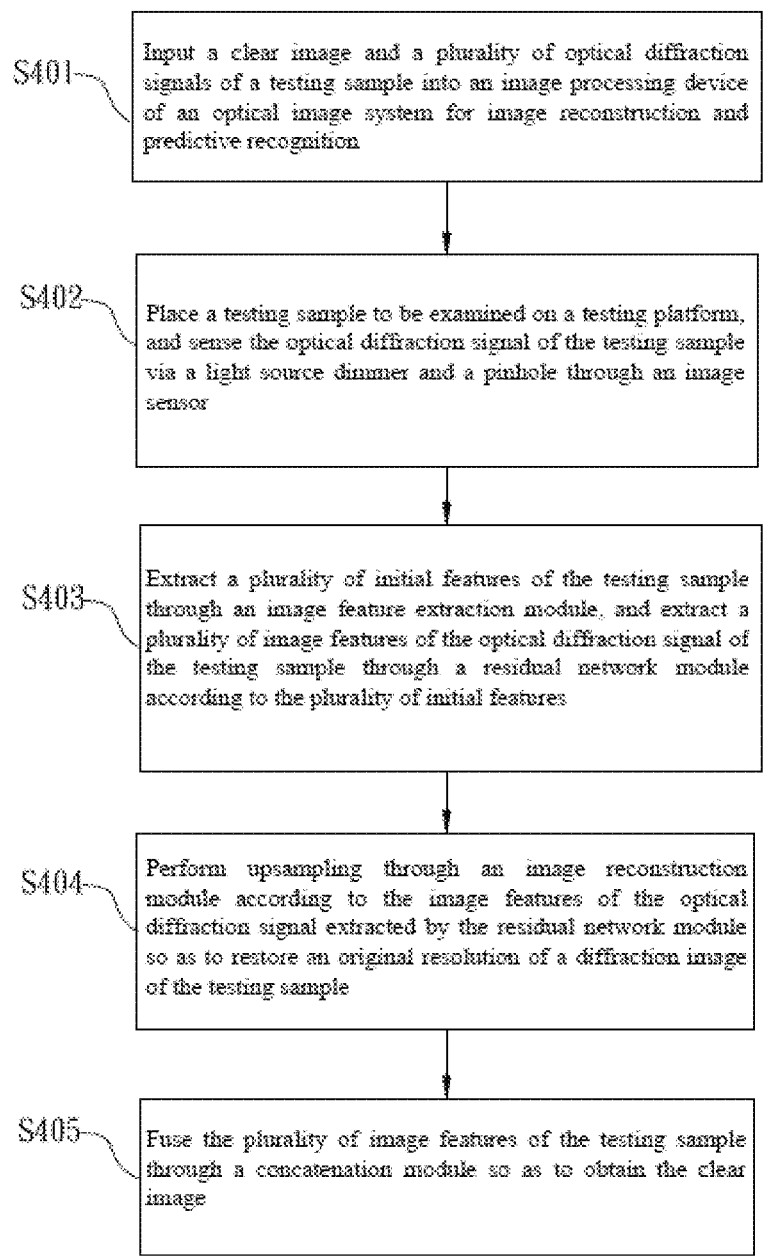
FIG. 4 is a flowchart of an optical image processing method using image restoration according to the present disclosure.

FIG. 4 is a step flowchart of an optical image processing method using image restoration according to the present disclosure. As shown in FIG. 4, in step S401, a clear image and a plurality of optical diffraction signals of a testing sample are input into an image processing device of an optical image system for image reconstruction and predictive recognition. In order to enable the image processing device of the present disclosure to have the effect of generating clear images similar to those generated by an optical microscope, it is necessary to perform a data learning and model training process of the image processing device. In the learning process of the image processing device, a large amount of image data is required, and therefore, it is necessary to perform model training on clear images of different testing samples and optical diffraction signals collected by the image sensor of the present disclosure, so as to improve the recognition.

In step S402, a testing sample to be examined is placed on a testing platform, and the optical diffraction signal of the testing sample is sensed via a light source dimmer and a pinhole through an image sensor. In the present disclosure, an optical imaging device is simplified by using the theory of scalar diffraction without the need of bulky and complex optical elements, it is only necessary to be composed of a non-coherent dimmer, a pinhole and an optical image sensor, the Field of View (FOV) size is not limited in the absence of a lens, a wide field of view (consistent with the area of the optical image sensor) and micron-scale image resolution can be achieved simultaneously, the optical diffraction signal is recorded on the sensor by controlling the spatial coherence of the light source, image reconstruction is performed by a mechanical learning algorithm without an optical lens, and an automatic recognition function can be implemented. According to the system for lensless optical image restoration and the calculation method of the present disclosure, a final image reconstruction result can be obtained in a short time.

In step S403, a plurality of initial features of the testing sample are extracted through an image feature extraction module, and a plurality of image features of the optical diffraction signal of the testing sample are extracted through a residual network module according to the plurality of initial features. In step S404, upsampling is performed through an image reconstruction module according to the image features of the optical diffraction signal extracted by the residual network module so as to restore an original resolution of the optical diffraction signal of the testing sample. Finally, in step S405, the plurality of image features of the testing sample are fused through a concatenation module so as to obtain the clear image. By image processing and image recognition as described above, the initial optical diffraction signal can be converted to the clear image similar to that generated by the optical microscope.

The present disclosure provides a system for lensless optical image restoration and an optical image processing method using image restoration, which have the functions of miniaturizing an optical microscopic system and greatly improving an image field of view, perform image reconstruction using a mechanical learning algorithm, can implement an automatic recognition function, and have considerable prospects and application value in the application of biomedical testing industry.

While the above implementations are preferred embodiments, the scope of implementation of the present disclosure cannot be limited thereto, and any equivalent changes or modifications made in accordance with the scope of patent application and the description of the present disclosure should all belong to the following patent coverage of the present disclosure.

DESCRIPTION OF SYMBOLS

10 Optical system
11 Light source
12 Pinhole
13 Testing platform
14 Image sensor
15 Image processing device
151 Image feature extraction module
152 Residual network module
153 Image reconstruction module
154 Concatenation module
31 Optical diffraction signal
32 Clear image
33 Image
S401-S405 Steps

The invention claimed is:

1. An optical system using image restoration, comprising:
a light source;
a pinhole, disposed on a light transmission path of the light source;
a testing platform, disposed on the light transmission path of the light source, the pinhole being located between the light source and the testing platform, and the testing platform being used to place a testing sample;
an image sensor, disposed below the testing platform, and used to sense the testing sample so as to output an optical diffraction signal; and
an image processing device, electrically connected to the image sensor and used to perform signal processing and optical signal recognition on the optical diffraction signal of the testing sample so as to obtain a clear image of the testing sample;
wherein the light source is a point light source composed of light emitting diodes, and the pinhole is composed of micron-sized optical pinholes or optical fibers;
wherein the testing sample is a biopsy or a blood smear;
wherein the image processing device further comprises:
an image feature extraction module, used to extract a plurality of initial features of the optical diffraction signal of the testing sample, when an optical diffraction signal is input, a downsampling is first performed twice, and the initial features are extracted through three parallel operation sub-networks using a convolution operation of step 2 to replace a traditional pooling layer;
a residual network module, connected to the image feature extraction module and used to extract a plurality of image features of the optical diffraction signal of the testing sample according to the plurality of initial features, and a parallel feature extraction is performed using a residual network as a backbone, and a dimension reduction is applied to extract advantageous features at a plurality of different scales;
an image reconstruction module, connected to the residual network module, and used to perform upsampling according to an image feature of an image extracted by the residual network module so as to restore an original resolution of the optical diffraction signal of the testing sample, and a transposed convolution is used for upsampling to progressively restore the original resolution; and a concatenation module, connected to the image reconstruction module, and used to fuse the plurality of image features of the testing sample and preserve more dimensional information for improved image clarity so as to obtain the clear image.

2. The optical system of claim 1, wherein the image feature extraction module performs downsampling on the optical diffraction signal, and a residual network has a convolutional layer, an activation layer and an addition layer.

3. The optical system of claim 2, wherein the image reconstruction module performs downsampling on the optical diffraction signal so as to restore the original resolution of the optical diffraction signal.

4. An optical image processing method using image restoration, comprising:
inputting a clear image and a plurality of optical diffraction signals of a testing sample into an image processing device of an optical image system for image reconstruction and predictive recognition;
placing a testing sample to be examined on a testing platform, and sensing the testing sample via a light source dimmer and a pinhole through an image sensor so as to output the optical diffraction signal;
extracting a plurality of initial features of the testing sample through an image feature extraction module, when an optical diffraction signal is input, a downsampling is first performed twice, and the initial features are extracted through three parallel operation sub-networks using a convolution operation of step 2 to replace a traditional pooling layer, and then extracting a plurality of image features of the optical diffraction signal of the testing sample through a residual network module according to the plurality of initial features, a parallel feature extraction is performed using a residual network as a backbone, and a dimension reduction is applied to extract advantageous features at a plurality of different scales, and performing upsampling through an image reconstruction module according to the plurality of image features of the optical diffraction signal extracted by the residual network module so as to restore an original resolution of the optical diffraction signal of the testing sample and a transposed convolution is used for upsampling to progressively restore the original resolution; and
fusing the plurality of image features of the testing sample through a concatenation module and preserve more dimensional information for improved image clarity so as to obtain the clear image.

5. The optical image processing method of claim 4, wherein the image feature extraction module performs downsampling on the optical diffraction signal so as to obtain the initial features of three sub-networks of the optical diffraction signal.

6. The optical image processing method of claim 4, wherein the residual network module comprises a convolutional layer, an activation layer and an addition layer, features of the optical diffraction signal are firstly searched by the convolutional layer, the activation layer outputs the optical diffraction signal to perform linear rectification conversion to overcome the problem of gradient disappearance, and the optical diffraction signals which are originally input and non-linearly transformed are finally superimposed on the addition layer.

7. The optical image processing method of claim 4, wherein the optical image processing method performs image processing of the optical diffraction signal using a convolutional neural network.

* * * * *